(12) United States Patent
Kishimoto et al.

(10) Patent No.: US 6,239,325 B1
(45) Date of Patent: May 29, 2001

(54) LOWER ALKANE OXIDATIVE DEHYDROGENATION CATALYSTS AND A PROCESS FOR PRODUCING OLEFINS

(75) Inventors: Nobuji Kishimoto; Etsushige Matsunami, both of Himeji (JP)

(73) Assignee: Nippon Shokubai Co Ltd, Osaka (JP)

( * ) Notice: Subject to any disclaimer, the term of this patent is extended or adjusted under 35 U.S.C. 154(b) by 0 days.

(21) Appl. No.: 09/313,658

(22) Filed: May 18, 1999

(30) Foreign Application Priority Data

May 18, 1998 (JP) .................................. 10-135418
May 18, 1998 (JP) .................................. 10-135419

(51) Int. Cl.$^7$ ...................................... C07C 5/32
(52) U.S. Cl. ........................ 585/658; 585/661; 585/662; 585/663; 562/521; 562/522; 562/545; 562/546; 562/547
(58) Field of Search ................... 502/305, 245; 585/658, 661, 662, 663, 654, 660, 652; 562/521, 522, 545, 546, 547

(56) References Cited

U.S. PATENT DOCUMENTS

| | | |
|---|---|---|
| 3,867,345 | 2/1975 | Koberstein et al. . |
| 3,923,819 | 12/1975 | Lussling et al. . |
| 4,131,631 | 12/1978 | Hardman . |
| 4,524,236 | 6/1985 | McCain . |
| 4,538,017 * | 8/1985 | Butler et al. ........................ 585/415 |
| 4,596,787 * | 6/1986 | Manyik et al. . |
| 4,709,071 * | 11/1987 | Sasaki et al. ........................ 558/322 |
| 4,754,091 * | 6/1988 | Jezl et al. ............................. 585/322 |
| 4,769,357 * | 9/1988 | Sarumar et al. ..................... 502/245 |
| 4,777,319 | 10/1988 | Kung et al. . |
| 5,162,578 * | 11/1992 | McCain, Jr. et al. .............. 562/512.2 |
| 5,210,293 * | 5/1993 | Kitson . |
| 5,510,558 * | 4/1996 | Umansky et al. ................... 585/658 |
| 5,739,392 | 4/1998 | Tanimoto et al. . |
| 5,744,015 * | 4/1998 | Mazanec et al. .................... 204/295 |
| 5,877,381 * | 3/1999 | Sasaki et al. . |

FOREIGN PATENT DOCUMENTS

| | | |
|---|---|---|
| 1073893A | 10/1992 | (CN) . |
| 0117146 | 8/1984 | (EP) . |
| 379433A1 | 7/1990 | (EP) . |
| 7-157462 * | 6/1995 | (JP) .......................... C07C/255/08 |
| 9736849 | 10/1997 | (WO) . |

OTHER PUBLICATIONS

Neftekhimiya (1990), 30(2), 207–10, and its English abstract.
J. Chem. Commun. (1991) (8) 558–9.
Catal. Lett. (1996), 37, (3,4), 241–6.
ACS Symp. Ser. (1996), 638 (Heterogeneous Hydrocarbon Oxidation) 155–169.
Japanese Laid–Open (Kokai) Pat. Appln. No. 245494/1996 and English abstract.
Japanese Kokai No. 045643/1998 and English abstract.
Japanese Kokai No. 118941/1998 and English abstract.
Japanese Kokai No. 62041/1980 and U.S. Patent No. 4,260,822.
Japanese Kokai No. 128247/1992 and English abstract.

* cited by examiner

*Primary Examiner*—Tom Dunn
*Assistant Examiner*—Christina Ildebrando

(57) ABSTRACT

The invention provides process for oxidative dehydrogenation of lower alkanes, by vapor phase oxidative dehydrogenation of $C_2$–$C_5$ lower alkanes in the presence of a catalyst and molecular oxygen to produce the corresponding olefins, in which the catalyst has a composition expressed by a general formula (1) below:

$$A_\alpha Sb_\beta W_\gamma D_\delta O x \quad (1)$$

in which A is at least one metal selected from the group consisting of molybdenum and chromium; Sb is antimony; W is tungsten; O is oxygen; and D is at least one metal selected from the group consisting of V, Nb, Ta, Fe, Co, Ni, Cu, Ag, Zn, B, Tl, Sn, Pb, Te, Li, Na, K, Rb, Cs, Mg, Ca, Sr, Ba, La, Ce and Sm; $\alpha$, $\beta$, $\gamma$, $\delta$ and x denote atomic numbers of A, Sb, W, D and O, respectively, where when $\alpha=1$, $\beta=0.5$–10, $\gamma=0.1$–10 and $\delta=0$–3; and x is a numerical value determined by the state of oxidation of those elements other than oxygen.

When these catalysts are used in reactions for oxidizing and dehydrogenating $C_2$–$C_5$ alkanes with molecular oxygen in vapor phase, corresponding olefins can be produced at high yield.

15 Claims, No Drawings

LOWER ALKANE OXIDATIVE DEHYDROGENATION CATALYSTS AND A PROCESS FOR PRODUCING OLEFINS

TECHNICAL FIELD TO WHICH THE INVENTION BELONGS

This invention relates to lower alkane oxidative dehydrogenation catalysts and a production process of olefins using said catalysts. More specifically, the invention relates to the catalysts which are suitable for use in vapor phase oxidative dehydrogenation of $C_2$–$C_5$ lower alkanes (hereinafter occasionally referred to simply as "lower alkanes") in the presence of molecular oxygen to produce corresponding olefins, and a process for oxydizing and dehydrogenating lower alkanes with molecular oxygen to produce corresponding olefins at high yields, with the use of said catalysts.

The invention also relates to a process for producing, from the olefins which have been obtained through vapor phase oxidative dehydrogenation of $C_2$–$C_5$ lower alkanes in the presence of molecular oxygen, the corresponding unsaturated aldehydes and/or unsaturated carboxylic acids.

PRIOR ART

As a production process for lower olefins, in particular, propylene and isobutene, simple dehydrogenation process of lower alkanes is recently reduced to industrial practice. However, this process is subject to an essential problem that it is difficult of giving high conversion due to the equilibrium limitation and furthermore requires high temperatures. Still in addition, deterioration of the catalyst within a short period is inavoidable in said process, which necessitates frequent regeneration of the catalyst using a switch converter or the like. In consequence, plant construction costs and utility costs for running the process are high and, depending on the conditions of location, it is unprofitable and its industrial application is restricted.

Whereas, attempts to produce lower olefins from lower alkanes through oxidative dehydrogenation which is free from the limitation by equlibrium have been-made since long, and various catalyst systems therefor have been proposed. Among those known, there are Co-Mo oxide catalyst (U.S. Pat. No. 4,131,631), V-Mg oxide catalyst (U.S. Pat. No. 4,777,319), Ni-Mo oxide catalyst (EP 379,433 A1) $CeO_2/CeF_3$ catalyst (CN 1,073,893A), Mg–Mo catalyst [*Neftekhimiya* (1990), 30(2) 207–10], $V_2O_5/Nb_2O_5$ catalyst [*J. Chem. Commun.* (1991) (8) 558–9], rare earth vanadates catalyst [*Catal. Lett.* (1996), 37, (3,4), 241–6] and $B_2O_3/Al_2O_3$ catalyst [*ACS Symp. Ser.* (1996), 638 (Heterogeneous Hydrocarbon Oxidation) 155–169). Those known catalysts, however, invariably show very low level oxidative dehydrogenation performance, the property of the prime importance, and are far short of industrial practice.

Japanese Laid-open (KOKAI) Patent Application, KOKAI No. 245494/1996 furthermore contains a disclosure on a process for further oxidizing propylene, which was formed through dehydrogenation of propane, to produce acrylic acid. This process, however, necessitates removal of the hydrogen formed during the dehydrogenation of propane from the reaction gas. Japanese KOKAI Nos. 045643/1998, 118491/1998, 62041/1980 and 128247/1992, etc. disclose processes for forming unsaturated aldehydes and/or acids from lower alkanes, in particular, acrolein and/or acrylic acid from propane and methacrolein and/or methacrylic acid from isobutane. However, yield of these object products indicated in these publications are very low, and the processes need to be improved in various aspects including the catalyst to be used.

THE PROBLEM TO BE SOLVED BY THE INVENTION

An object of this invention is to provide novel oxidative dehydrogenation catalysts useful for vapor phase oxidative dehydrogenation of lower alkanes with molecular oxygen to produce corresponding lower olefins at high yield; and also to provide a process for producing from lower alkanes the corresponding olefins at high yield, by the use of said catalysts.

Another object of the invention is to provide a process for producing from lower alkanes corresponding unsaturated aldehydes and/or unsaturated carboxylic acids at high yield.

MEANS FOR SOLVING THE PROBLEM

We have made concentrative studies in search of the catalysts suitable for oxidizing and dehydrogenating lower alkanes with molecular oxygen to produce the corresponding lower olefins, to discover that a catalyst containing molybdenum and/or chromium, antimony and tungsten as the indispensable components, or a catalyst in which said catalytically active components are supported on a refractory inorganic carrier exhibit excellent oxidative dehydrogenation performance; and that lower olefins could be produced at high yield with the use of said catalyst. The present invention has been completed based on these discoveries.

Thus, the present invention provides catalysts for oxidative dehydrogenation of lower alkanes, said catalysts being suitable for use in vapor phase oxidative dehydrogenation of $C_2$–$C_5$ lower alkanes in the presence of molecular oxygen to produce corresponding olefins and characterized by having a composition expressed by a general formula (1) below:

$$A_\alpha Sb_\beta W_\gamma D_\delta O_x \tag{1}$$

(in which A is at least one metal selected from the group consisting of molybdenum and chromium; Sb is antimony; W is tungsten; O is oxygen; and D is at least one metal selected from the group consisting of V, Nb, Ta, Fe, Co, Ni, Cu, Ag, Zn, B, Tl, Sn, Pb, Te, Li, Na, K, Rb, Cs, Mg, Ca, Sr, Ba, La, Ce and Sm; $\alpha$, $\beta$, $\gamma$, $\delta$ and x denote atomic numbers of A, Sb, W, D and 0, respectively, where when $\alpha=1$, $\beta=0.5$–10, $\gamma=0.1$–10 and $\delta=0$–3; and x is a numerical value determined by the state of oxidation of those elements other than oxygen).

The present invention furthermore provides a process for producing olefins which comprises vapor phase oxidative dehydrogenation of $C_2$–$C_5$ lower alkanes in the presence of molecular oxygen to form corresponding olefins, characterized by the use of the above-described catalyst.

According to the present invention, furthermore, a process for producing, from lower alkane, unsaturated aldehyde and unsaturated acid at high yield is provided, in which an olefin obtained through vapor-phase oxidative dehydrogenation of $C_2$–$C_5$ lower alkanes in the presence of molecular oxygen using the above-defined catalyst is further oxidized at vapor phase in the presence of oxygen to provide unsaturated aldehyde and unsaturated acid.

The invention moreover provides a process for producing unsaturated acid from lower alkane at high yield, in which the unsaturated aldehyde obtained as above is further oxidized at vapor phase in the presence of molecular oxygen to provide unsaturated acid.

EMBODIMENTS OF THE INVENTION

More specifically, $C_2$–$C_5$ lower alkanes signify ethane, propane, n-butane, isobutane, n-pentane and isopentane. The catalysts of the present invention are used in oxidative dehydrogenation reactions of these lower alkanes to produce corresponding olefins, more specifically, ethylene from ethane, propylene from propane, n-butene from n-butane, isobutene from isobutane, n-pentene from n-pentane and isopentene from isopentane. These lower alkanes may be used either singly or as a mixture of more than one. The oxidative dehydrogenation catalysts of the present invention are useful for the production of, in particular, propylene and isobutene from propane and isobutane, respectively.

Referring to the general formula (1), the catalysts in which, when $\alpha=1$, $\beta=1-5$, $\gamma=0.2-5$ and $\delta=0-0.5$ are preferred. Inter alia, those in which when $\alpha=1$, $\beta=1-3$, $\delta=0.3-3$ and $\delta=0-0.3$ exhibit most favorable performance.

Also the catalysts containing, as the component D referring to general formula (1), V, Nb, K, Mg, Sn, Fe, Co or Ni are preferred. In particular, the catalysts containing V exhibit most favorable performance.

Accordingly, oxidative dehydrogenation catalysts represented by the following general formula (2) are exemplified as one embodiment of the present invention:

$$A_\alpha Sb_\beta W_\gamma V_\delta E_\epsilon O x \qquad (2)$$

[in which A is at least one metal selected from the group consisting of molybdenum and chromium; Sb is antimony; W is tungsten; V is vanadium; O is oxygen; and E is at least one metal selected from the group consisting of Nb, Ta, Fe, Co, Ni, Cu, Ag, Zn, B, Tl, Sn, Pb, Te, Li, Na, K, Rb, Cs, Mg, Ca, Sr, Ba, La, Ce, and Sm (preferably consisting of Nb, K, Mg, Sn, Fe, Co and Ni); $\alpha$, $\beta$, $\gamma$, $\delta$, $\epsilon$ and x denote atomic numbers of A, Sb, W, V, E and O, respectively, where when a=1, $\beta=0.5-10_{10}$ (preferably 1-5, inter alia, 1-3), $\gamma=0.1-10$ (preferably 0.2-5, inter alia, 0.3-3), $\delta=0.01-3$ (preferably 0.01-0.5); and $\epsilon=0-3$ (preferably 0-0.5, inter alia, 0-0.3); and x is a numerical value determined by the state of oxidation of those elements other than oxygen].

The oxidative dehydrogenation catalysts of general formula (1) of the present invention may be used as supported on a refractory inorganic carrier for the purpose of improving activity level and physical durability. As the refractory inorganic carrier, those generally used in preparation of this type of catalysts can be used, the representative examples thereof including silica, alumina, titania, zirconia, silica-alumina, silica-titania and silica-zirconia. In particular, silica-alumina is the most advantageous, because it gives higher yield of object products. The ratio of silica to alumina in the silica-alumina catalyst system normally ranges from 10–90% by weight to 90–10% by weight. The amount of the catalytically active component to be carried is normally between 10 and 90% by weight of the refractory inorganic carrier.

The method of preparation of the oxidative dehydrogenation catalysts of the present invention is not subject to any critical limitations, but any of conventionally practiced methods or known methods for preparation of this type of catalysts can be used. For example, the catalysts may be prepared by the procedures comprising dissolving ammonium paramolybdate and/or chromium-nitrate in pure water under heating; adding thereto an aqueous solution of ammonium metatungstate and then antimony trioxide in powder form and if necessary an aqueous solution containing a compound of at least one metal selected from the group consisting of V, Nb, Ta, Fe, Co, Ni, Cu, Ag, Zn, B, Tl, Sn, Pb, Te, Li, Na, K, Rb, Cs, Mg, Ca, Sr, Ba, La, Ce and Sm; and if desired further adding a carrier such as silica, alumina, and the like; condensing the resulting mixture under heating and stirring for a fixed period; drying the resulting slurry; and thereafter firing the same at 300°–800° C.

The firing atmosphere is subject to no limitation, and the firing may be conducted in air, an atmosphere of high or low oxygen concentration, an inert gas such as nitrogen, helium, argon or the like, the reaction gas or in vacuum.

The starting materials for catalyst preparation are not critical, but may be any of nitrate, oxide, hydroxide, chloride, carbonate, acetate, oxygen acid, ammonium salt of oxygen acid, etc. of the elements used.

Again the use form of refractory inorganic carrier is subject to no critical limitation, which allows versatile selection according to the form of use of the catalyst, such as, besides molded products, powder of oxide or hydroxide, gel or sol.

The starting gas to be used in carrying out the vapor-phase oxidative dehydrogenation reaction of the present invention may contain, besides the lower alkane or alkanes and molecular oxygen, a diluent gas if necessary. As the source of molecular oxygen, air or pure oxygen is used. Molecular oxygen is normally used at a ratio of 0.1 to 5 mols per mol of lower alkanes. As the diluent gas, an inert gas such as nitrogen, helium or carbon dioxide or steam is conveniently used.

The reaction conditions for carrying out the vapor phase oxidative dehydrogenation of the present invention are subject to no critical limitation. For example, the starting gas as described above is contacted with an oxidative dehydrogenation catalyst of the present invention under such conditions as: at a space velocity of 300–10,000 $hr^{-1}$ and at a temperature between 250° and 650° C. While the reaction is normally conducted under atmospheric pressure, a reduced or elevated pressure may be used. The reaction system again is not critical, which may be a fixed bed system, moving bed system or fluidized bed system. It may also be one-pass system or recycling system.

The olefines (alkenes) which are obtained through the vapor phase oxidative dehydrogenation of $C_2$–$C_5$ lower alkanes (alkane oxidative dehydrogenation step) using the catalyst of the present invention can be further oxidized to produce unsaturated aldehydes and unsaturated acids (alkene oxidation step). The unsaturated aldehydes can further be oxidized to produce unsaturated acids (aldehyde oxidation step). Thus formed unsaturated aldehydes and/or unsaturated acids are trapped with an absorption column (absorbing step). As the oxygen source in the present invention, air and/or oxygen produced by such methods as cryogenic method, P.S.A. (pressure swing adsorption) method and the like can be used. According to the present invention, it is possible to form from lower alkanes the corresponding olefins, without side-production of hydrogen. If necessary oxygen and/or steam may be added to the gases to be introduced in each of the above steps, and such additional oxygen and/or steam are supplied by, for example, air, above-described oxygen, water and/or the gas discharged of said absorbing step.

As one specific example of useful catalyst in the alkene oxidation step, those expressed by following general formula (3) may be named:

$$Mo_a Bi_b Fe_c A_d B_e C_f D_g O_x \qquad (3)$$

in which Mo is molybdenum; Bi is bismuth; Fe is iron; A is at least one element selected from the group consisting of cobalt and nickel; B is at least one element selected from the group consisting of alkali metals and thallium; C is at least one element selected from the group consisting of silicon, aluminium, zirconium and titanium; D is at least one element selected from the group consisting of tungsten, phosphorus, tellurium, antimony, tin, cerium, lead, niobium, manganese, arsenic and zinc; and O is oxygen: and the ratio of those elements is, when a=12, b=0.1–10, c=0.1–20, d=2–20, e=0.001–10, f=0–30, g=0–4 and x is a numerical value determined by the state of oxidation of those elements other than oxygen.

Also as one specific example of useful catalyst in the aldehyde oxidation step, those expressed by following general formula (4) may be named:

$$Mo_h V_i W_j E_k F_l G_m H_n O_x \tag{4}$$

in which Mo is molybdenum; V is vanadium; W is tungsten; E is at least one element selected from the group consisting of copper, cobalt, bismuth and iron; F is at least one element selected from the group consisting of antimony and niobium; G is at least one element selected from the group consisting of silicon, aluminium, zirconium and titanium; H is at least one element selected from the group consisting of alkaline earth metals, thallium, phosphorus, tellurium, tin, cerium, lead, manganese and zinc; and O is oxygen: and the ratio of those elements is, when h=12, i=0.1–10, j=0–10, k=0.1–20, l=0–10, m=0–10, n=0–30, and x is a numerical value determined by the state of oxidation of those elements other than oxygen.

EFFECT OF THE INVENTION

The lower alkane oxidative dehydrogenation catalysts according to the present invention excel in the oxidative dehydrogenation ability and enable the production from lower alkanes of corresponding olefins at high yield.

Also according to the present invention, unsaturated aldehyde and/or unsaturated acid can be produced from lower alkanes stably at high yield.

EXAMPLES

Hereinafter the invention is explained in further details referring to working examples, in which percentages are by weight, unless otherwise specified, and the conversion, one-pass yield and selectivity are indicated following the definitions below, inclusive of the side products:

$$\text{conversion (mol \%)} = \frac{\text{(mol number of reacted lower alkane)}}{\text{(mol number of fed lower alkane)}} \times 100$$

$$\text{selectivity (mol \%)} = \frac{\text{(mol number of each of formed compounds)}}{\text{(mol number of reacted lower alkane)}} \times$$

$$\frac{\text{(carbon number of each of formed compounds)}}{\text{(carbon number of fed lower alkane)}} \times 100$$

one-pass yield (mol %) =

$$\frac{\text{(mol number of each of formed compounds)}}{\text{(mol number of fed lower alkane)}} \times$$

$$\frac{\text{(carbon number of each of formed compounds)}}{\text{(carbon number of fed lower alkane)}} \times 100$$

Example 1

A 1-liter beaker was charged with 109.4 g of alumina sol A-200 (Nissan Chemical Industries, Co., Al$_2$O$_3$ concentration: 10.5%), 16.0 g of silica sol Snowtex N (Nissan Chemical Industries, Co., SiO$_2$ concentration: 20.5%) and 150 ml of water, and the content was heated to about 80° C. under stirring. Separately, in a 500-ml beaker 100 ml of water was added to 1.77 g of ammonium paramolybdate [(NH$_4$)Mo$_7$O$_{24}$·4H$_2$O: Wako Pure Chemical Industry, Ltd., special grade reagent] to dissolve it under heating and stirring. To the solution, 8.35 g of aqueous ammonium metatungstate [(NH$_4$)$_6$H$_2$W$_{12}$O$_{48}$] solution MW-2 (Nippon Inorganic Colour and Chemical Co., Ltd.), containing 50% of WO$_3$] as diluted with 50 ml of water was added, followed by further addition of 3.07 g of Sb$_2$O$_3$ powder (Wako Pure Chemical Industry, Ltd., purity 99.9%) as dispersed in 100 ml of water with homogenizer, and 2 hours' stirring at about 80° C. while the liquid level was maintained constant. The resulting suspension was gradually added to the above-prepared alumina-silica sol mixture slurry dropwise, followed by further 2 hours' stirring at 80° C. while the liquid level was maintained constant. Thereafter the heating temperature was raised to 90° C. and stirring was continued for about 4 hours to concentrate the system by evaporation of water content. So obtained paste was dried at 120° C. for 14 hours and then fired in atmospheric air at 650° C. for 3 hours. The composition of the resulting catalyst was as follows:

37% (Mo$_1$Sb$_{2.1}$W$_{1.8}$O$_x$)/[49% (Al$_2$O$_3$)–14% (SiO$_2$)].

In the above, the brackets [ ] denote the carrier component, as also in the subsequent examples.

Particle size of the above catalyst was uniformized to 9–20 mesh, and 2.8 g of which was packed in an ordinary flow type reactor. The oxidative dehydrogenation reaction of the invention was carried out under the following conditions. The results were as shown in Table 1.

Reaction gas: C$_3$H$_8$/O$_2$/N$_2$=1/1/8 (molar ratio)

Feed rate: 112.5 ml/min.

SV: 2,000 hr$^{-1}$ (In the subsequent Examples, indication of SV is omitted. As the catalyst weight was constant, SV underwent fluctuation more or less dependent on its packing density.)

Reaction temperature: 540° C.

Example 2

A 1-liter beaker was charged with 109.4 g of alumina sol A-200 (Nissan Chemical Industries, Co.) 16.0 g of silica sol Snowtex N (Nissan Chemical Industries, Co.) and 150 ml of water, and the content was heated to about 80° C. under stirring. Separately, in a 500-ml beaker 100 ml of water was added to 1.77 g of ammonium paramolybdate (Wako Pure Chemical Industry, Ltd., special grade reagent) to dissolve it under heating and stirring. To the resulting solution, 9.27 g of aqueous ammonium metatungstate solution MW-2 (Nippon Inorganic Colour and Chemical Co., Ltd.) as diluted with 50 ml of water was added, followed by further addition of 0.14 g of ammonium metavanadate (Wako Pure Chemical Industry, Ltd., special grade reagent) as dissolved in 50 ml of water under heating, and 3.65 g of Sb$_2$O$_3$ powder (Wako Pure Chemical Industry, Ltd., purity 99.9%) as dispersed in 100 ml of water with homogenizer, by the order stated. The system was stirred for 2 hours at about 80° C., while the liquid level was maintained constant. The resulting suspension was gradually added to the above-prepared alumina-silica sol mixture slurry dropwise, followed by further 2 hours' stirring at 80° C. while the liquid level was maintained constant. Thereafter the heating temperature was raised to 90° C. and stirring was continued for about 4 hours to concentrate the system by evaporation of water content.

So obtained paste was dried and fired under identical conditions with those in Example 1. The composition of the resulting catalyst was as follows:

40% $(Mo_1Sb_{2.5}W_{2.0}V_{0.12}O_x)/[47\%$ $(Al_2O_3)-13\%$ $(SiO_2)]$.

Using this catalyst, the reaction was carried out under identical conditions with those employed in Example 1, except that the reaction temperature was changed to 500° C. The results were as shown in Table 1.

Example 3

A catalyst was prepared in the same manner as in Example 2, except that the amount of the ammonium paramolybdate was changed to 1.34 g, that of the aqueous ammonium metatungstate solution MW-2, to 8.77 g, that of the ammonium metavanadate, to 0.22 g and that of the $Sb_2O_3$ powder, to 3.31 g. The composition of the resulting catalyst was as follows:

40% $(Mo_1Sb_{3.0}W_{2.5}V_{0.25}O_x)/[47\%$ $(Al_2O_3)-13\%$ $(SiO_2)]$.

Using this catalyst, the reaction was carried out under identical conditions with those of Example 1, except that the reaction temperature was changed to 500° C. The results were as shown in Table 1.

Example 4

A catalyst was prepared in the same manner as in Example 2, except that the ammonium metavanadate was replaced with 2.60 g of niobium oxalate (CBMM Co., containing 20.5% of $Nb_2O_5$ upon conversion) as dissolved in 50 ml of water. The composition of the resulting catalyst was as follows:

41% $(Mo_1sb_{2.5}W_{2.0}Nb_{0.4}O_x)/[46\%$ $(Al_2O_3)-13\%$ $(SiO_2)]$.

Using this catalyst, the reaction was carried out under identical conditions with those of Example 1, except that the reaction temperature was changed to 520° C. The results were as shown in Table 1.

Example 5

A catalyst was prepared in the same manner as in Example 2, except that the ammonium metavanadate was replaced with 0.58 g of nickel nitrate $[Ni(NO_3)_3 \cdot 6H_2O$, Wako Pure Chemical Industry, Ltd., purity 99.9%] as dissolved in 50 ml of water. The composition of the resulting catalyst was as follows:

40% $(Mo_1Sb_{2.5}W_{2.0}Ni_{0.2}O_x)/[47\%$ $(Al_2O_3)-13\%$ $(SiO_2)]$.

Using this catalyst, the reaction was carried out under identical conditions with those of Example 1. The results were as shown in Table 1.

Example 6

A catalyst was prepared in the same manner as in Example 2, except that the ammonium metavanadate was replaced with 0.51 g of magnesium nitrate $[Mg(NO_3)_2 \cdot 6H_2O$, Wako Pure Chemical Industry, Ltd., special grade reagent] as dissolved in 50 ml of water. The composition of the resulting catalyst was as follows:

40% $(Mo_1Sb_{2.5}W_{2.0}Mg_{0.2}O_x)/[47\%$ $(Al_2O_3)-13\%$ $(SiO_2)]$.

Using this catalyst, the reaction was carried out under identical conditions with those of Example 1. The results were as shown in Table 1.

Example 7

A catalyst was prepared in the same manner as in Example 2, except that the ammonium metavanadate was replaced with 0.27 g of stannous oxide powder (SnO, Wako Pure Chemical Industry, Ltd., purity 99.9%) as dissolved in 50 ml of water. The composition of the resulting catalyst was as follows:

40% $(Mo_1Sb_{2.5}W_{2.0}Sn_{0.2}O_x)/[47\%$ $(Al_2O_3)-13\%$ $(SiO_2)]$.

Using this catalyst, the reaction was carried out under identical conditions with those of Example 1. The results were as shown in Table 1.

Comparative Example 1

A catalyst was prepared in the same manner as in Example 1, except that use of the $Sb_2O_3$ powder was omitted. The composition of the resulting catalyst was as follows:

28% $(Mo_1W_{1.8}O_x)/[56\%$ $(Al_2O_3)-16\%$ $(SiO_2)]$.

Using this catalyst, the reaction was run under identical conditions with those of Example 1, except that the reaction temperature was changed to 510° C. The results were as shown in Table 1.

Comparative Example 2

A catalyst was prepared in the same manner as in Example 1, except that use of the ammonium metatungstate was omitted. The composition of the resulting catalyst was as follows:

23% $(Mo_1Sb_{2.1}O_x)/[60\%$ $(Al_2O_3)-17\%$ $(SiO_2)]$.

Using this catalyst, the reaction was run under identical conditions with those of Example 1. The results were as shown in Table 1.

Comparative Example 3

A catalyst was prepared in the same manner as in Example 2, except that the amount of the alumina sol A-200 was changed to 64.5 g; that of the silica sol Snowtex N, to 9.44 g; that of the aqueous ammonium metatungstate solution MW-2, to 6.95 g; and that of $Sb_2O_3$ powder, to 2.19 g. The composition of the resulting catalyst was as follows:

40% $(Mo_1Sb_{15}W_{15}O_x)/[47\%$ $(Al_2O_3)-14\%$ $(SiO_2)]$.

Using the above catalyst, the reaction was carried out under identical conditions with those of Example 1. The results were as shown in Table 1.

TABLE 1

| | Reaction temp. (° C.) | Propane conversion (mol %) | Selectivity (mol %) | | Propylene one-pass yield (mol %) |
|---|---|---|---|---|---|
| | | | propylene | acrolein | |
| Example 1 | 540 | 29.7 | 35.0 | 2.0 | 10.4 |
| Example 2 | 500 | 30.8 | 42.5 | 2.7 | 13.1 |
| Example 3 | 500 | 32.0 | 39.8 | 2.5 | 12.7 |
| Fxample 4 | 520 | 30.6 | 36.1 | 2.2 | 11.0 |
| Example 5 | 540 | 31.2 | 34.8 | 2.3 | 10.9 |
| Example 6 | 540 | 29.4 | 36.0 | 2.1 | 10.6 |
| Example 7 | 540 | 31.5 | 34.1 | 2.0 | 10.7 |
| Comparative Example 1 | 510 | 27.7 | 10.5 | 0.6 | 2.8 |
| Comparative Example 2 | 540 | 23.8 | 13.8 | 1.7 | 3.3 |
| Comparative Example 3 | 540 | 12.5 | 33.2 | 2.1 | 4.1 |

Example 8

Example 2 was repeated except that propane was replaced with isobutane to produce isobutene. That is, an ordinary flow type reactor was charged with 2.8 g of the catalyst as used in Example 2 of 9–20 mesh in size, and through which a reaction gas composed of i—$C_4H_{10}/O_2/N_2$=1/1/8 (molar ratio) was passed at a rate of 112.5 ml/min. The reaction temperature was 500° C.

The results were as follows: isobutane conversion=29.8 mol % isobutene selectivity=28.5 mol % methacrolein selectivity=2.0 mol % one-pass yield of isobutene=8.5 mol %.

Example 9

Catalysts were prepared in the same manner as in Example 7 except that they contained iron, cobalt or manganese, respectively, instead of tin. Those catalysts were used in the reaction run under identical conditions with those of Example 7, to produce similar results.

Example 10

A 1-liter beaker was charged with 29.3 g of alumina sol A-200, 15.0 g of silica sol Snowtex N and 50 ml of water, and the content was heated to about 80° C. under stirring, followed by addition of 24.0 g of chromium nitrate [$Cr(NO_3)_3 \cdot 9H_2O$, Wako Pure Chemical Industry, Ltd., special grade reagent] as dissolved in 100 ml of water. In succession thereto, 13.9 g of aqueous ammonium metatungstate solution MW-2 as diluted with 50 ml of water and 13.1 g of the $Sb_2O_3$ powder as dispersed in 100 ml of water with homogenizer were added to the system by the order stated, and then the whole system was stirred for 2 hours at about 80° C., while maintaining the constant liquid level. Thereafter the heating temperature was raised to 90° C. and stirring was continued for about 4 hours to concentrate the system by evaporation of water content. So obtained paste was dried at 120° C. for 14 hours and then fired in nitrogen atmosphere for 3 hours at 580° C. The composition of the resulting catalyst was as follows:

80% 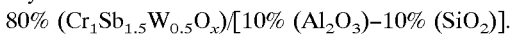

Particle size of the above catalyst was uniformized to 9–20 mesh, and 2.8 g of which was packed in an ordinary flow type reactor. The oxidative dehydrogenation reaction of the invention was carried out under the following conditions. The results were as shown in Table 2.

Reaction gas: $C_3H_8/O_2/N_2$=1/1/8 (molar ratio)
Feed rate: 112.5 ml/min
SV: 3,100 hr$^{-1}$ (In the subsequent Examples, indication of SV is omitted. As the catalyst weight was constant, SV underwent fluctuation more or less dependent on its packing density.)
Reaction temperature: 530° C.

Example 11

A catalyst was prepared in the same manner as in Example 10, except that 0.351 g of ammonium meta-vanadate ($NH_4VO_3$, Wako Pure Chemical Industry, Ltd., special grade reagent) as dissolved in 50 ml of water under heating was added after the addition of the aqueous ammonium metatungstate solution and before the addition of the $Sb_2O_3$ powder dispersion. The composition of the resulting catalyst was as follows:

80% 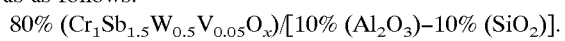

Using this catalyst, the reaction was carried out under identical conditions with those of Example 10, except that the reaction temperature was changed to 500° C. The results were as shown in Table 2.

Example 12

A catalyst was prepared in the same manner as in Example 11, except that the amount of ammonium metavanadate was changed to 1.05 g. The composition of the resulting catalyst was as follows:

80% ($Cr_1Sb_{1.5}W_{0.5}V_{0.15}O_x$)/[10% ($Al_2O_3$)–10% ($SiO_2$)].

Using this catalyst, the reaction was carried out under identical conditions with those of Example 10, except that the reaction temperature was changed to 480° C. The results were as shown in Table 2.

Example 13

A catalyst was prepared in the same manner as in Example 11, except that the ammonium metavanadate was replaced with 0.31 g of magnesium nitrate [$Mg(NO_3)_2 \cdot 6H_2O$, Wako Pure Chemical Industry, Ltd., special grade reagent] as dissolved in 50 ml of water. The composition of the resulting catalyst was as follows:

80% 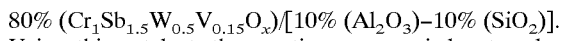

Using this catalyst, the reaction was run under identical conditions with those of Example 10. The results were as shown in Table 2.

Example 14

A catalyst was prepared in the same manner as in Example 11, except that the ammonium metavanadate was replaced with 0.30 g of potassium nitrate ($KNO_3$, Wako Pure Chemical Industry, Ltd., special grade reagent) as dissolved in 50 ml of water. The composition of the resulting catalyst was as follows:

80% 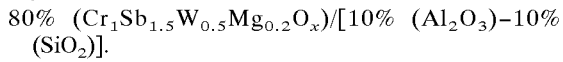

Using this catalyst, the reaction was run under identical conditions with those of Example 10, except that the reaction temperature was changed to 540° C. The results were as shown in Table 2.

Example 15

A 1-liter beaker was charged with 182.6 g of the silica sol Snowtex N and 100 ml of water, and the content was heated to about 80° C. under stirring. Under continued stirring, further 4.00 g of chromium nitrate (Wako Pure Chemical Industry, Ltd., special grade reagent) as dissolved in 50 ml of water was added, followed by addition of 2.32 g of the aqueous ammonium metatungstate solution MW-2 as diluted with 50 ml of water, 0.058 g of ammonium metavanadate as dissolved in 50 ml of water under heating, and 2.18 g of the $Sb_2O_3$ powder as dispersed in 100 ml of water with homogenizer, by the order stated. The system was stirred for 2 hours at about 80° C., while the liquid level was maintained constant. Thereafter the heating temperature was raised to 90° C. and stirring was continued for about 4 hours to concentrate the system by evaporation of water content. So obtained paste was dried at 120° C. for 14 hours and then fired in nitrogen atmosphere at 580° C. for 3 hours. The composition of the resulting catalyst was as follows:

10% 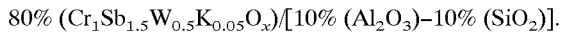

Using this catalyst, the reaction was run under identical conditions with those of Example 10, except that the reaction temperature was changed to 500° C. The results were as shown in Table 2.

Example 16

A catalyst was prepared in the same manner as in Example 15, except that the ammonium metavanadate was replaced with 1.30 g of niobium oxalate (CBMM Co., containing 20.5 % of $Nb_2O_5$ upon conversion) as dissolved in 50 ml of water. The composition of the resulting catalyst was as follows:

10% 

Using this catalyst, the reaction was carried out under identical conditions with those of Example 10. The results were as shown in Table 2.

Example 17

A catalyst was prepared in the same manner as in Example 15, except that the ammonium metavanadate was replaced with 0.81 g of iron nitrate [Fe(NO$_3$)$_3$·9H$_2$O, Wako Pure Chemical Industry, Ltd., special grade reagent] as dissolved in 50 ml of water. The composition of the resulting catalyst was as follows:

10% (Cr$_1$Sb$_{1.5}$W$_{0.5}$Fe$_{0.2}$O$_x$)/[90% (SiO$_2$)].

Using this catalyst, the reaction was carried out under identical conditions with those of Example 10. The results were as shown in Table 2.

Example 18

A 1-liter beaker was charged with 24.0 g of chromium nitrate (Wako Pure Chemical Industry, Ltd., special grade reagent) as dissolved in 100 ml of water, followed by further addition of 13.9 g of the aqueous ammonium metatungstate solution MW-2 as diluted with 50 ml of water, 1.40 g of ammonium metavanadate as dissolved in 50 ml of water under heating, and 17.5 g of the Sb$_2$O$_3$ powder, as dispersed in 100 ml of water with homogenizer, by the order stated. The system was stirred for 2 hours at about 80° C., while the liquid level was maintained constant. Thereafter the heating temperature was raised to 90° C. and stirring was continued for about 4 hours to concentrate the system by evaporation of water content. So obtained paste was dried at 120° C. for 14 hours and then fired in nitrogen atmosphere at 580° C. for 3 hours. The composition of the resulting catalyst was as follows:

Cr$_1$Sb$_2$W$_{0.5}$V$_{0.2}$O$_x$.

Using this catalyst, the reaction was carried out under identical conditions with those employed in Example 10 except that the reaction temperature was changed to 540° C. The results were as shown in Table 2.

Comparative Example 4

A catalyst was prepared in the same manner as in Example 10, except that no chromium nitrate was used. The composition of the resulting catalyst was as follows:

76.6% (Sb$_3$W$_1$O$_x$)/[11.7% (Al$_2$O$_3$)–11.7% (SiO$_2$)].

Using this catalyst, the reaction was carried out under identical conditions with those of Example 10, except that the reaction temperature was changed to 540° C. The results were as shown in Table 2.

Comparative Example 5

A catalyst was prepared in the same manner as in Example 10, except that no Sb$_2$O$_3$ was used. The composition of the resulting catalyst was as follows:

65.2% (Cr$_1$W$_{0.5}$O$_x$)/[17.4% (Al$_2$O$_3$)–17.4% (SiO$_2$)].

Using this catalyst, the reaction was carried out under identical conditions with those of Example 10. The results were as shown in Table 2.

Comparative Example 6

A catalyst was prepared in the same manner as in Example 10, except that no aqueous ammonium meta-tungstate solution was used. The composition of the resulting catalyst was as follows:

74.2% (Cr$_1$Sb$_{1.5}$O$_x$)/[12.9% (Al$_2$O$_3$)–12.9% (SiO$_2$)].

Using this catalyst, the reaction was carried out under identical conditions with those of Example 10. The results were as shown in Table 2.

Comparative Example 7

A catalyst was prepared in the same manner as in Example 10, except that the amount of Sb$_2$O$_3$ was changed to 61.1 g. The resulting catalyst had the following composition:

92.2% (Cr$_1$Sb$_7$W$_{0.5}$O$_x$)/[3.9% (Al$_2$O$_3$)–3.9% (SiO$_2$)].

Using this catalyst, the reaction was carried out under identical conditions with those of Example 10, except that the reaction temperature was changed to 540° C. The results were as shown in Table 2.

Comparative Example 8

A catalyst was prepared in the same manner as in Example 10, except that the amount of the aqueous ammonium metatungstate solution was changed to 139.0 g. The composition of the resulting catalyst was as follows:

93.4% (Cr$_1$Sb$_{1.5}$W$_5$O$_x$)/[3.3% (Al$_2$O$_3$)–3.3% (SiO$_2$)].

Using this catalyst, the reaction was carried out under identical conditions with those of Example 10, except that the reaction temperature was changed to 540° C. The results were as shown in Table 2.

TABLE 2

| | Reaction temp. (° C.) | Propane conversion (mol %) | Selectivity (mol %) | | Propylene one-pass yield (mol %) |
|---|---|---|---|---|---|
| | | | propylene | acrolein | |
| Example 10 | 530 | 31.7 | 38.2 | 2.7 | 12.1 |
| Example 11 | 500 | 33.9 | 45.5 | 3.1 | 15.5 |
| Example 12 | 480 | 32.2 | 45.3 | 2.9 | 14.6 |
| Example 13 | 530 | 33.5 | 39.3 | 2.8 | 13.2 |
| Example 14 | 540 | 31.8 | 39.0 | 2.9 | 12.4 |
| Example 15 | 500 | 34.6 | 40.9 | 1.3 | 14.1 |
| Example 16 | 530 | 32.3 | 38.7 | 1.4 | 12.5 |
| Example 17 | 530 | 33.8 | 36.7 | 1.3 | 12.4 |
| Example 18 | 540 | 28.5 | 35.1 | 2.5 | 10.0 |
| Comparative Example 4 | 540 | 9.6 | 31.2 | 4.3 | 3.0 |
| Comparative Example 5 | 500 | 26.5 | 14.3 | 0.3 | 3.8 |
| Comparative Example 6 | 530 | 30.8 | 14.0 | 2.0 | 4.3 |
| Comparative Example 7 | 540 | 15.2 | 33.7 | 3.8 | 5.1 |
| Comparative Example 8 | 540 | 28.3 | 15.5 | 2.6 | 4.4 |

Example 19

Example 11 was repeated except that propane was replaced with isobutane to produce isobutene. That is, an ordinary flow type reactor was packed with 2.8 g of the catalyst as used in Example 11 of 9–20 mesh in size, and through which a reaction gas composed of i—C$_4$H$_{10}$/O$_2$/N$_2$=1/1/8 (molar ratio) was passed at a rate of 112.5 ml/min. The reaction temperature was 500° C.

The results were as follows: isobutane conversion=27.7 mol % isobutene selectivity=30.7 mol % methacrolein selectivity=3.5 mol % one-pass yield of isobutene=8.5 mol %.

Example 20

Catalysts were prepared in the same manner as in Example 17 except that they contained tin, cobalt or nickel, respectively, instead of iron. Those catalysts were used in the reaction run under identical conditions with those of Example 17, to produce similar results.

Example 21

Each independently temperature-controllable single-pipe flow type reactors (A), (B) and (C) were connected in such a manner that gas would flow by the order of (A) to (B) to (C), with the piping so designed that the gas formed in the reactor (C) is introduced into an absorption column to allow absorption of condensed component and introduction of the uncondensed gas flowing out of the absorption column into the reactor (A) through its gas inlet portion, and the reaction was conducted with the following particulars. The piping also was so connected that fresh air could be introduced into the reactor (B) through its gas inlet portion.

(Preparation of catalyst)

8 g of the catalyst as used in Example 2 was packed in the reactor (A), while the reactor (B) was packed with 32 g of a catalyst of the following composition (excepting oxygen) as described in Example 1 of Japanese Patent Publication No. 42241/1972:

$Mo_{10}Co_4Bi_1Fe_1W_2Si_{1.35}K_{0.05}$.

The reactor (C) was packed with 52 g of a catalyst of the following composition (excepting oxygen) as described in Example 1 of Japanese KOKAI No. 206504/1996:

$Mo_{12}V_{6.1}W_1Cu_{2.3}Sb_{1.2}$.

The flow rates of propane, air and recovered gas from absorption column were so controlled at the gas inlet portion of the reactor (A) as to give the reaction gas composition of 15 vol % $C_3H_8$, 15 vol % $O_2$ and 70 vol % of inert gases comprising nitrogen, carbon oxide, etc. In that occasion, the space velocity to the oxidative dehydrogenation catalyst was 3000 hr$^{-1}$. The product gas from the reactor (A) was fed into the reactor (B) while adding air thereto at such a rate that $O_2/C_3H_6$ ratio therein should become 3.0 at the entrance portion of the reactor (B), and the product gas from the reactor (B) was fed into the reactor (C). The reaction temperatures in the reactors (A), (B) and (C) during the run were 490° C., 325° C. and 250° C., respectively.

Analysis of the product gas from the reactor (C) indicated: $C_3H_8$ conversion, 42.3 mol % and acrylic acid yield, 19.0 mol %.

Example 22

(Preparation of catalyst)

12.5 g of the catalyst as used in Example 11 was packed in the reactor (A). Otherwise the reaction was carried out in the identical manner with Example 21.

Analysis of the product gas from the reactor (C) showed $C_3H_8$ conversion, 46.5 mol % and acrylic acid yield of 20.6 mol %.

What is claimed is:

1. A process for selectively producing olefins which comprises oxidizing and dehydrogenating $C_2$–$C_5$ lower alkanes in the presence of molecular oxygen in vapor phase to produce corresponding olefins which comprises contacting said $C_2$–$C_5$ lower alkanes and said molecular oxygen in vapor phase with a catalyst, wherein said catalyst consists essentially of a composition expressed by the formula (1) below:

$$A_\alpha Sb_\beta W_\gamma D_\delta Ox \qquad (1)$$

in which A is at least one metal selected from the group consisting of molybdenum and chromium; Sb is antimony; W is tungsten; O is oxygen; and D is at least one metal selected from the group consisting of V, Nb, Ta, Fe, Co, Ni, Cu, Ag, Zn, B, Tl, Sn, Pb, Te, Li, Na, K, Rb, Cs, Mg, Ca, Sr, Ba, La, Ce and Sm; α, β, γ, δ and x denote atomic numbers of A, Sb, W, D and O, respectively, where when α=1, β=1–5, γ=0.2–5 and γ=0–3; and x is a numerical value determined by the state of oxidation of those elements other than oxygen.

2. A process according to claim 1 in which, when α=1, β=1–3, γ=0.3–3 and δ=0–0.3, referring to the formula (1).

3. A process according to claim 1, in which the $C_2$–$C_5$ lower alkanes are mixed with a gas consisting essentially of molecular oxygen and contacted with the catalyst.

4. A process for selectively producing unsaturated $C_2$ to $C_5$ aldehyde and $C_2$ to $C_5$ unsaturated acid from $C_2$ to $C_5$ lower alkane which comprises oxidizing and dehydrating $C_2$ to $C_5$ lower alkane to obtain $C_2$ to $C_5$ olefin by contacting a $C_2$ to $C_5$ lower alkane and a gas consisting essentially of molecular oxygen in vapor phase at about atmospheric pressure with a catalyst, wherein said catalyst consists essentially of a composition expressed by the formula (1) below:

$$A_\alpha Sb_\beta W_\gamma D_\delta Ox \qquad (1)$$

in which A is at least one metal selected from the group consisting of molybdenum and chromium; Sb is antimony; W is tungsten; O is oxygen; and D is at least one metal selected from the group consisting of V, Nb, K, Mg, Sn, Fe, Co and Ni, α, β, γ, δ and x denote atomic numbers of A, Sb, W, D and O, respectively, where when α=1, β=1–5, γ=0.2—less than 5 and δ=0–0.5, and x is a numerical value determined by the state of oxidation of those elements other than oxygen, and contacting the thus obtained $C_2$–$C_5$ olefins in vapor phase with molecular oxygen to obtain the $C_2$ to $C_5$ aldehyde and $C_2$ to $C_5$ unsaturated acid.

5. A process for selectively producing a $C_2$ to $C_5$ unsaturated acid from $C_2$ to $C_5$ lower alkane according to claim 4 which comprises contacting the unsaturated $C_2$ to $C_5$ aldehyde in the presence of molecular oxygen to produce the $C_2$ to $C_5$ unsaturated acid.

6. A process for selectively producing olefins which comprises oxidizing and dehydrogenating $C_2$–$C_5$ lower alkanes in the presence of molecular oxygen in vapor phase to produce corresponding olefins which comprises contacting said $C_2$–$C_5$ lower alkanes and said molecular oxygen in vapor phase with a catalyst, wherein said catalyst consists essentially of a composition expressed by the formula (1):

$$A_\alpha Sb_\beta W_\gamma D_\delta Ox \qquad (1)$$

in which A is molybdenum; Sb is antimony; W is tungsten; O is oxygen; and D is at least one metal selected from the group consisting of V, Nb, K, Mg, Sn, Fe, Co and Ni; α, β, γ, δ and x denote atomic numbers of A, Sb, W, D and O, respectively, where when α=1, β=1–5, γ=0.2 to less than 5 and δ=0–0.5; x is a numerical value determined by the state of oxidation of those elements other than oxygen.

7. A process according to claim 6, in which, when α=1, β=1–3, γ=0.3–3 and δ=0–0.3, referring to the formula (1).

8. A process according to claim in which the $C_2$–$C_5$ lower alkanes are mixed with a gas consisting essentially of molecular oxygen and contacted with the catalyst.

9. A process for selectively producing unsaturated $C_2$ to $C_5$ aldehyde and $C_2$ to $C_5$ unsaturated acid from $C_2$ to $C_5$ lower alkane which comprises oxidizing and dehydrating $C_2$ to $C_5$ lower alkane to obtain $C_2$ to $C_5$ olefin by contacting a $C_2$ to $C_5$ lower alkane and a gas consisting essentially of molecular oxygen in vapor phase at about atmospheric pressure with a catalyst, wherein said catalyst consists essentially of a composition expressed by a general formula (1) below:

  (1)

in which A is molybdenum; Sb is antimony; W is tungsten; O is oxygen; and D is at least one metal selected from the group consisting of V, Nb, K, Mg, Sn, Fe, Co and Ni, $\alpha$, $\beta$, $\gamma$, and x denote atomic numbers of A, Sb, W, D and O, respectively, where when $\alpha=1$, $\beta=1-5$, $\gamma=0.2$-less than 5 and $\delta=0-0.5$, and x is a numerical value determined by the state of oxidation of those elements other than oxygen, and contacting the thus obtained $C_2$–$C_5$ olefins in vapor phase with molecular oxygen to obtain the $C_2$ to $C_5$ aldehyde and $C_2$ to $C_5$ unsaturated acid.

10. A process for selectively producing a $C_2$ to $C_5$ unsaturated acid from $C_2$ to $C_5$ lower alkane according to claim 9 which comprises contacting the unsaturated $C_2$ to $C_5$ aldehyde in the presence of molecular oxygen to produce the $C_2$ to $C_5$ unsaturated acid.

11. A process for selectively producing olefins which comprises oxidizing and dehydrogenating $C_2$–$C_5$ lower alkanes in the presence of molecular oxygen in vapor phase to produce corresponding olefins which comprises contacting said $C_2$–$C_5$ lower alkanes and said molecular oxygen in vapor phase with a catalyst, wherein said catalyst consists essentially of a composition expressed by the formula (1):

  (1)

in which A is chromium; Sb is antimony; W is tungsten; O is oxygen; and D is at least one metal selected from the group consisting of V, Nb, K, Mg, Sn, Fe, Co and Ni; $\alpha$, $\beta$, $\gamma$, $\delta$ and x denote atomic numbers of A, Sb, W, D and O, respectively, where when $\alpha=1$, $\beta=1-5$, $\gamma=0.2$ to less than 5 and $\delta=0-0.5$; and x is a numerical value determined by the state of oxidation of those elements other than oxygen.

12. A process according to claim 11, in which, when $\alpha=1$, $\beta=1-3$, $\gamma=0.3-3$ and $\delta=0-0.3$, referring to the formula (1).

13. A process according to claim 12, in which the $C_2$–$C_5$ lower alkanes are mixed with a gas consisting essentially of molecular oxygen and contacted with the catalyst.

14. A process for selectively producing unsaturated $C_2$ to $C_5$ aldehyde and $C_2$ to $C_5$ unsaturated acid from $C_2$ to $C_5$ lower alkane which comprises oxidizing and dehydrating $C_2$ to $C_5$ lower alkane to obtain $C_2$ to $C_5$ olefin by contacting a $C_2$ to $C_5$ lower alkane and a gas consisting essentially of molecular oxygen in vapor phase at about atmospheric pressure with a catalyst, wherein said catalyst consists essentially of a composition expressed by the formula (1) below:

  (1)

in which A is chromium; Sb is antimony; W is tungsten; O is oxygen; and D is at least one metal selected from the group consisting of V, Nb, K, Mg, Sn, Fe, Co and Ni, $\alpha$, $\beta$, $\gamma$, $\delta$ and x denote atomic numbers of A, Sb, W, D and O, respectively, where when $\alpha=1$, $\beta=1-5$, $\gamma=0.2$-less than 5 and $\delta=0-0.5$, and x is a numerical value determined by the state of oxidation of those elements other than oxygen, and contacting the thus obtained $C_2$–$C_5$ olefins in vapor phase with molecular oxygen to obtain the $C_2$ to $C_5$ aldehyde and $C_2$ to $C_5$ unsaturated acid.

15. A process for selectively producing a $C_2$ to $C_5$ unsaturated acid from $C_2$ to $C_5$ lower alkane according to claim 14 which comprises contacting the unsaturated $C_2$ to $C_5$ aldehyde in the presence of molecular oxygen to produce the $C_2$ to $C_5$ unsaturated acid.

* * * * *